(12) United States Patent  
Teodorczyk et al.

(10) Patent No.: US 7,943,022 B2  
(45) Date of Patent: May 17, 2011

(54) ANALYTE TEST STRIP WITH IMPROVED REAGENT DEPOSITION

(75) Inventors: Maria Teodorczyk, San Jose, CA (US); Remedios Dato, Pleasanton, CA (US); Koon-wah Leong, Sunnyvale, CA (US)

(73) Assignee: Lifescan, Inc., Milpitas, CA (US)

( * ) Notice: Subject to any disclaimer, the term of this patent is extended or adjusted under 35 U.S.C. 154(b) by 924 days.

(21) Appl. No.: 11/849,949

(22) Filed: Sep. 4, 2007

(65) Prior Publication Data

US 2009/0057146 A1  Mar. 5, 2009

(51) Int. Cl.  
*G01N 27/26* (2006.01)  
*G01N 33/487* (2006.01)

(52) U.S. Cl. .......... 204/403.11; 204/403.01; 205/777.5; 205/792

(58) Field of Classification Search ..... 204/400–403.15; 205/777.5, 787, 792; 600/309–367; 422/68.1–98; 436/62–71, 500–548; 435/4–40.52  
See application file for complete search history.

(56) References Cited

U.S. PATENT DOCUMENTS

| | | | |
|---|---|---|---|
| 4,301,353 A | 11/1981 | Suenaga et al. | |
| 5,653,918 A | 8/1997 | Towlson | |
| 5,708,247 A | 1/1998 | McAleer | |
| 6,046,051 A | 4/2000 | Jina | |
| 6,179,979 B1 | 1/2001 | Hodges et al. | |
| 6,309,526 B1 | 10/2001 | Fujiwara et al. | |
| 6,716,577 B1 * | 4/2004 | Yu et al. | 435/6 |
| 6,875,327 B1 * | 4/2005 | Miyazaki et al. | 204/403.14 |
| 7,073,246 B2 | 7/2006 | Bhullar et al. | |
| 2004/0060818 A1 * | 4/2004 | Feldman et al. | 204/403.01 |
| 2004/0244151 A1 * | 12/2004 | Sakata et al. | 23/306 |
| 2004/0245121 A1 | 12/2004 | Nagakawa et al. | |
| 2005/0023137 A1 * | 2/2005 | Bhullar et al. | 204/403.1 |
| 2005/0096409 A1 | 5/2005 | Davies et al. | |

FOREIGN PATENT DOCUMENTS

| | | |
|---|---|---|
| EP | 1 571 442 A1 | 9/2005 |
| EP | 1 577 665 A1 | 9/2005 |
| EP | 1783486 A1 | 5/2007 |
| WO | WO 95/22881 A1 | 8/1995 |
| WO | WO 99/30152 A1 | 6/1999 |
| WO | WO 01/67099 | 9/2001 |
| WO | WO 01/73124 | 10/2001 |
| WO | WO 2004/039600 A2 | 5/2004 |

(Continued)

OTHER PUBLICATIONS

Harvey et al., "*Fabrication Techniques and Their Applications to Produce Novel Micromachined Structures and Devices Using Excimer Laser Projection*", Exitech Ltd., Hanborough Park, Long Hanborough, Oxford, UK, SPIE vol. 3223, 1997, 8 pgs.

(Continued)

*Primary Examiner* — Alexa D Neckel  
*Assistant Examiner* — Jennifer Dieterle

(57) ABSTRACT

An analyte, system, strip and method are described. In one example, an analyte test strip is provided that includes a substrate, electrically conductive material and an isolated portion of the electrically conductive material. The substrate has a generally planar surface that extends from a first end to a second end. The electrically conductive material is disposed on the generally planar surface to define a plurality of electrodes spaced apart from each other. The isolated portion of the electrically conductive material is disposed between at least two electrodes so that the isolated portion is not in electrical communication with the plurality of electrodes.

19 Claims, 8 Drawing Sheets

FOREIGN PATENT DOCUMENTS

| | | |
|---|---|---|
| WO | WO 2004/039897 A2 | 5/2004 |
| WO | WO 2004/040005 A1 | 5/2004 |
| WO | WO 2004/040285 A1 | 5/2004 |
| WO | WO 2004/040287 A1 | 5/2004 |
| WO | WO 2004/040290 A1 | 5/2004 |
| WO | WO 2004/040948 A1 | 5/2004 |

OTHER PUBLICATIONS

M.C. Gower, *Excimer lasers: current and future applications in industry and medicine*, Laser Processing in Manufacture, Chapman & Hall, London, 1993, 42 pages.

Pethig, et al., *Development of biofactory-on-a-chip technology using excimer laser micromachining*, J. Micromech. Microeng. 8 (1998) 57-63, UK.

Rizvi, et al. *An Excimer Laser Micromachining System for the production of Bioparticle Electromanipulation Devices*, Exitech Ltd., Hanborough Park, Long Hanborough, Oxford, UK, SPIE vol. 3224, 1997, 7 pgs.

Rizvi, et al., *Direct Manufacture of Miniature Bio-Particle Electro-Manipulation Devices using Excimer Laser Mask Projection Techniques*, Exitech Ltd., Hanborough Park, Long Hanborough, Oxford, UK, 1998, 5 pgs.

* cited by examiner

US 7,943,022 B2

ANALYTE TEST STRIP WITH IMPROVED REAGENT DEPOSITION

BACKGROUND

Electrochemical methods and devices for determining analyte concentrations in fluid samples find wide application in the treatment and management of medical conditions such as diabetes. Individuals suffering from diabetes monitor their blood glucose concentrations using such methods often several times per day.

Electrochemical methods generally rely upon the correlation between a current, a potential or accumulated charge and the concentration of analyte, typically in conjunction with a reagent that produces charge carriers when combined with the analyte. The electrochemical biosensors for performing the tests are typically disposable test strips having a reagent disposed thereon that chemically reacts with a biological fluid such as blood. The test strip is mated to a test meter such that the test meter can measure the reaction between the analyte and the reagent to determine the concentration of the analyte. For electrochemically-based test strips, the electrical signal is transferred to the meter through electrical contact pads on the test strips and contacts within the meter strip port connector.

A known technique of manufacturing a test strip involves using a metallized polymeric film and forming a conductive electrode pattern on the film. The electrode pattern can be formed by a suitable etching process, including laser ablation or chemical etching, to remove the conductive material from the film leaving in place a conductive electrode pattern interlaced with exposed substrate material. The electrode pattern therefore is defined by a gap of exposed film or substrate material between the conductive material.

Applicants have discovered that on certain prototype test strips made via the laser ablation processes, deposition of the reagent on the electrode pattern was not uniform. Applicants have also discovered that on such prototype test strips, the ability of an analyte sample to consistently fill the reagent and electrode sensing area via the capillary effect was poor. Applicants believe that these issues would lead to a poorly performing test strip.

SUMMARY

Applicants have resolved these issues by implementation of various technical features to provide for various embodiments of the present invention not heretofore available in the art. In one aspect, an analyte test strip is provided that includes a substrate, electrically conductive material and an isolated portion of the electrically conductive material. The substrate has a generally planar surface that extends from a first end to a second end. The electrically conductive material is disposed on the generally planar surface to define a plurality of electrodes spaced apart from each other. The isolated portion of the electrically conductive material is disposed between at least two electrodes so that the isolated portion is not in electrical communication with the plurality of electrodes.

In another aspect, an analyte measurement system for measuring a concentration of an analyte in a fluid sample is provided. The system includes a meter and a test strip. The meter includes an electronic circuit for applying a test voltage between the reference electrode and the working electrode and a signal processor. The test includes a substrate having a reference electrode and a working electrode that are separated by an isolated portion of electrically conductive material so that capillary action is assisted during filling of the test strip with the fluid sample.

In a further aspect, a test strip for measuring a concentration of an analyte in a fluid sample is provided. The test strip includes a substrate material. A reference electrode is disposed on the substrate with a first working electrode proximate the reference electrode. A second working electrode is disposed on the substrate proximate the first working electrode. An isolated portion of electrically conductive material is located proximal to one of the first and second working electrodes and distal to the reference electrode.

In yet a further aspect, a method of making an analyte test strip is provided. The method can be achieved by depositing a layer of a conductive material on a substrate; and removing selective portions of the layer of conductive material to define a plurality of electrodes with at least an electrically isolated island of conductive material separated from any of the electrodes at a distance of about 50 microns or less to electrically isolate the island from the electrodes.

These and other embodiments, features and advantages will become apparent to those skilled in the art when taken with reference to the following more detailed description of the invention in conjunction with the accompanying drawings that are first briefly described herebelow.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (in which like numerals represent like elements), of which.

DETAILED DESCRIPTION

It is noted that the following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient", "host" and "subject" refer to any human or animal subject and are not intended to limit the systems or methods to human use, although use of the subject invention in a human patient represents a preferred embodiment.

Figure 1B:
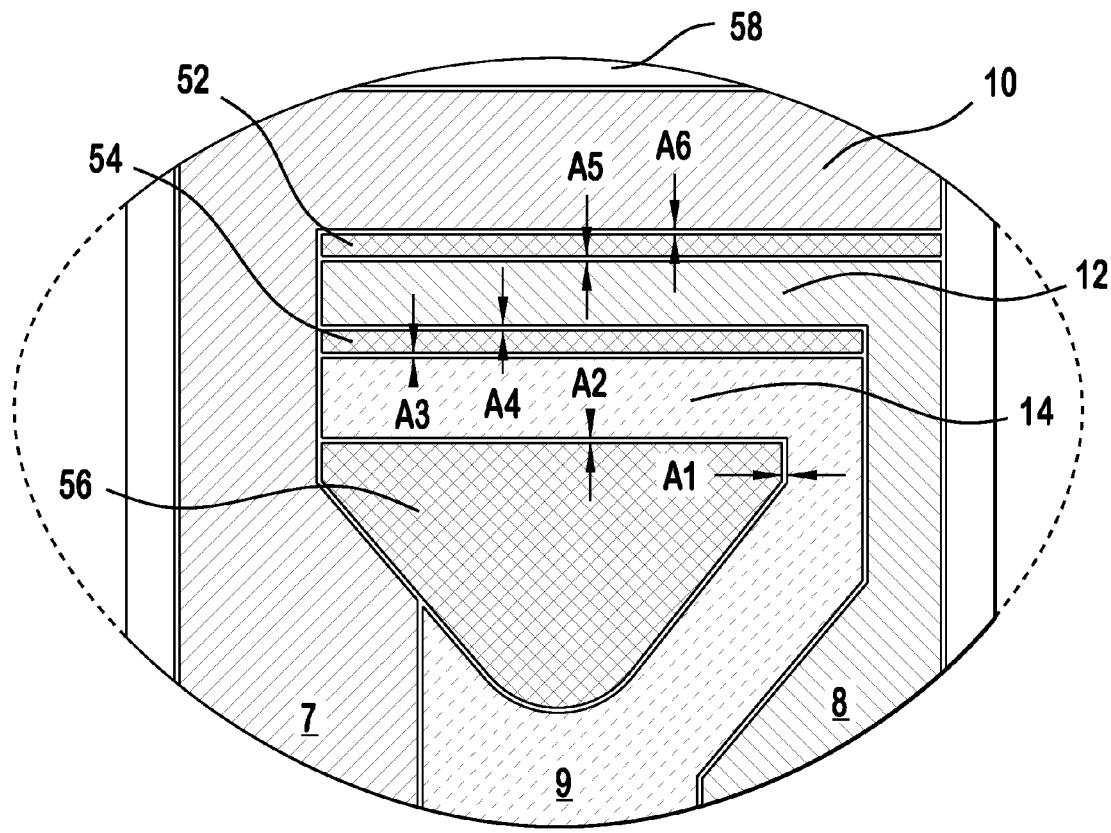
FIG. 1B illustrates a close-up top down view of one end of the test strip of FIG. 1A.
Figure 1A:
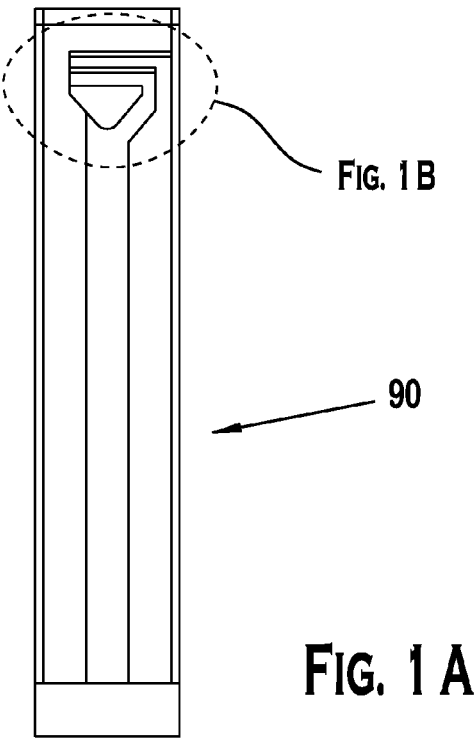
FIG. 1A illustrates an exemplary embodiment of the test strip.
Figure 1C:
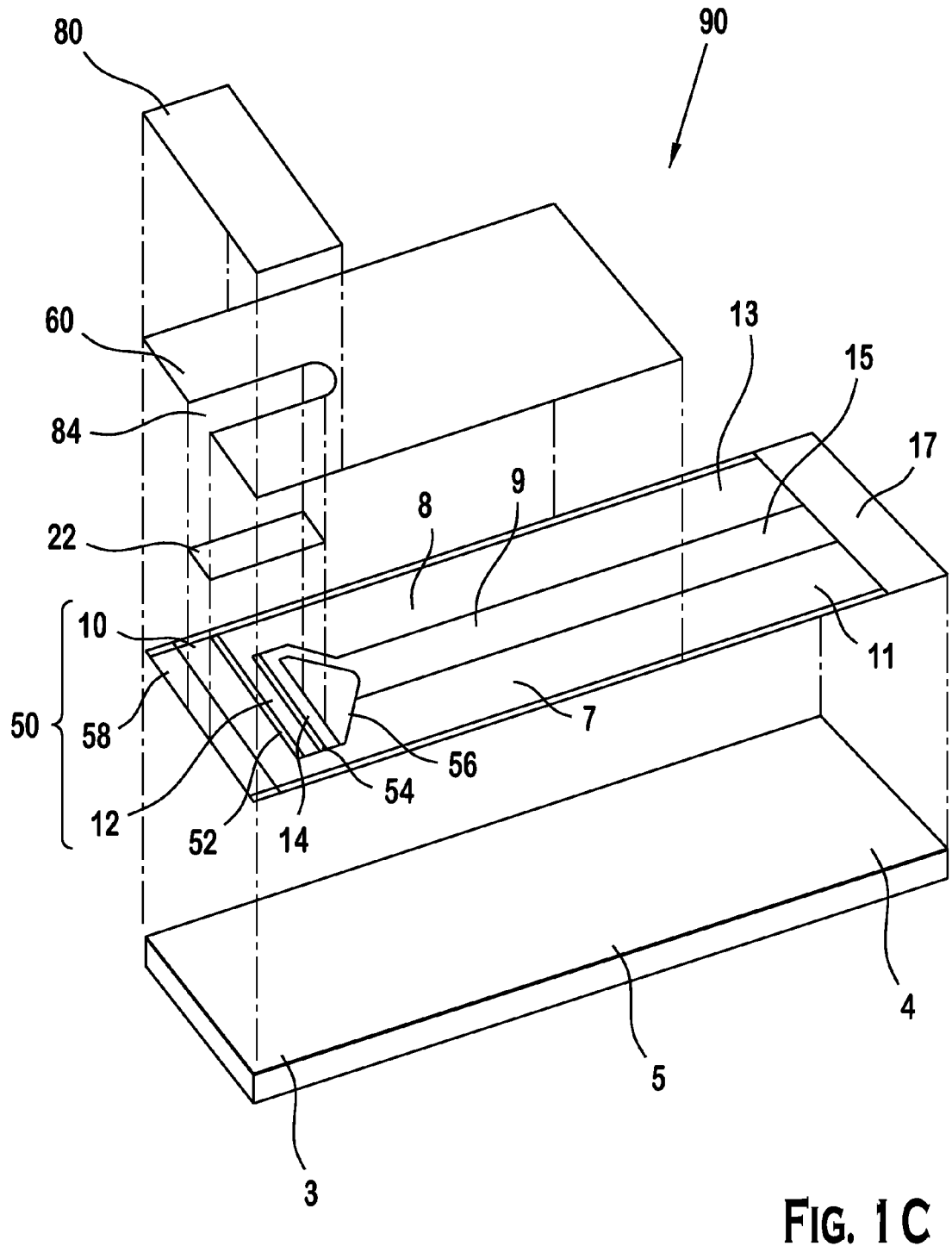
FIG. 1C is a top exploded perspective view of a test strip according to an exemplary embodiment.
Figure 1D:
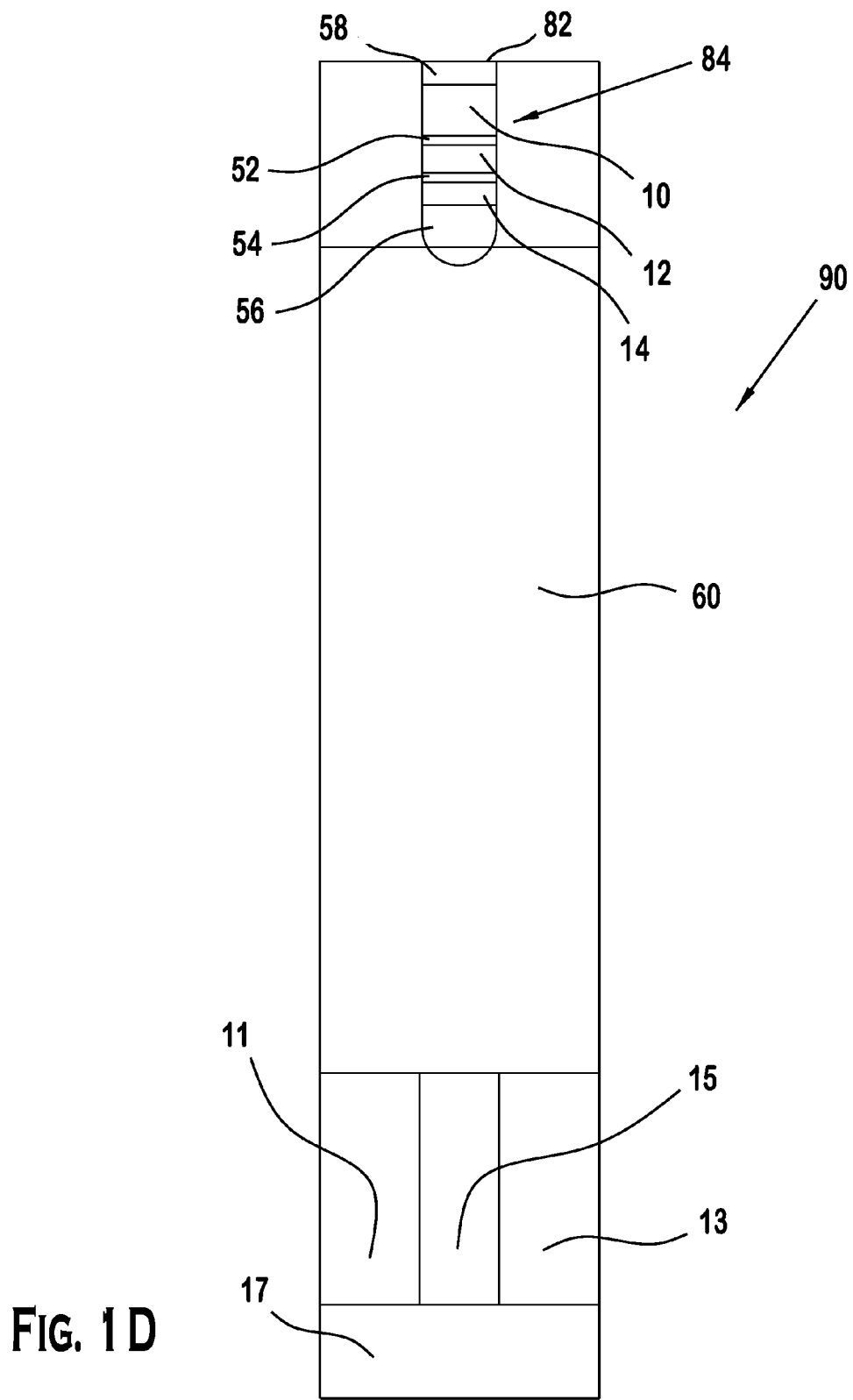
FIG. 1D is a top view of the test strip illustrated in FIG. 1C after it has been assembled.
Figure 1E:
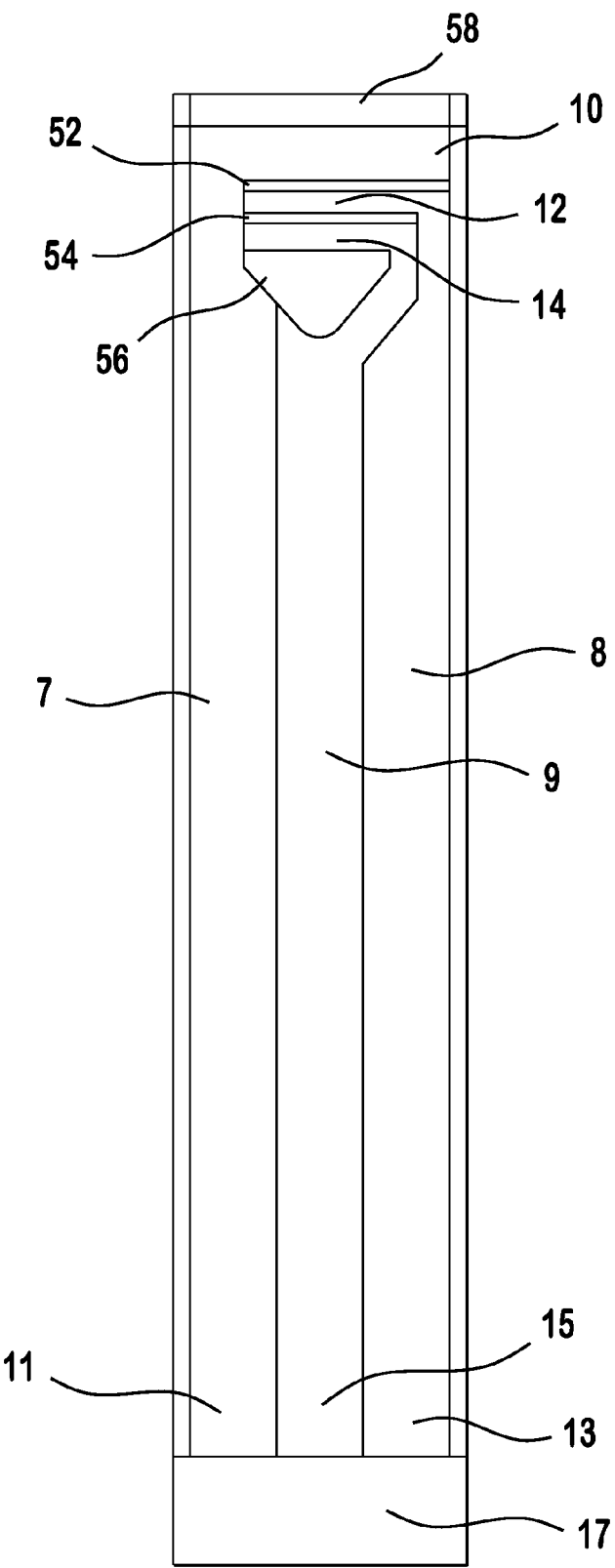
FIG. 1E is a top view of the conductive layer of the test strip illustrated in FIGS. 1A and 1B according to an exemplary embodiment.

FIGS. 1A and 1E illustrate an exemplary embodiment in which a test strip 90 is provided having a first end 3 and second end 4. The first (or distal) end 3 includes a biosensing portion shown in FIG. 1B. The second (or proximal) end 4 includes an electrical contact portion.

In FIG. 1B, the biosensing portion is provided with three electrodes 10, 12, and 14, respectively. The electrodes can be of generally the same conductive material. Between the electrodes 10 and 12, there is provided a first electrically isolated island 52. Similarly, a second electrically isolated island 54 is provided between electrodes 12 and 14. Likewise, a third electrically isolated island 56 is provided distal to the third electrode 14 and nearer to the proximal portion 4. Each of the conductive islands 52, 54, and 56 can be made of generally the same electrically conductive material as one or more of the electrodes. Further, each of the "islands" is intended to be electrically isolated from the electrodes 10, 12, and 14 of the test strip 90.

As shown in FIG. 1C, the test strip 90 can be made by a layering a plurality of discrete components on a substrate. Specifically, these layers may include a conductive layer 50, a reagent layer 22, a spacer layer 60 and a top layer or cover 80 having a hydrophilic adhesive coating. Test strip 90 may be manufactured in a series of steps in which the conductive layer 50 and reagent layer 22 are sequentially deposited on substrate 5 using, for example, a screen printing process as described in U.S. Pre-Grant Publication No. US20050096409A1 and published International Application Nos. WO2004040948A1, WO2004040290A1, WO2004040287A1, WO2004040285A2, WO2004040005A1, WO2004039897A2, and WO2004039600A2. In an alternative embodiment, an ink jetting process may be used to deposit reagent layer 22 on substrate 5. An example ink jetting process is described in U.S. Pat. No. 6,179,979. Yet another alternative process for depositing reagent 22 onto conductive layer 50 includes a drop-on-demand process. Spacer layer 60 and top layer 80 may be taken from a roll stock and laminated onto substrate 5. In an alternative embodiment, a sputtering process is used to apply conductive layer 50 and patterns are created in conductive layer 50 by laser ablation, laser etching or scribing by mechanical means such that less than 10% or, more typically, less than 6% of the conductive layer 50 on the surface is removed. Test strip 90 includes a distal end 3 and a proximal end 4 as shown in FIGS. 1C and 1D.

The fully assembled test strip 90, as shown in FIG. 1D, includes an inlet 82 through which a blood sample may be drawn into a sample-receiving chamber 84. Inlet 82 may be formed by cutting through a distal portion 3 of test strip 90. A blood sample can be applied to inlet 82 to fill sample receiving chamber 84 so that glucose can be measured. The side edges of a U-shaped opening in spacer layer 60 located adjacent to reagent layer 22 each define a wall of sample receiving chamber 84. A bottom portion or "floor" of sample receiving chamber 84 includes a portion of substrate 5 and conductive layer 50. A top portion or "roof" of sample receiving chamber 84 includes distal top layer 80.

For test strip 90, as shown in FIGS. 1A, 1B, 1C and 1D, conductive layer 50 includes a reference electrode 10, a first working electrode 12, a second working electrode 14, a reference contact pad 11, a first contact pad 13, a second contact pad 15 and a strip detection contact pad 17. Reference contact pad 11, first contact pad 13, second contact pad 15 and strip detection contact pad 17 provide electrical connection to a test meter to allow for data and measurement collection.

Conductive layer 50 also includes a first isolated portion 52, a second isolated portion 54 and an optional third isolated portion 56. First isolated portion 52 and second isolated portion 54 facilitate uniform reagent coating by minimizing the surface area of exposed substrate 5 that is hydrophobic. Third isolated portion 56 may be any shape (e.g., triangular) and facilitates filling of test strip 90 by providing a capillary force to draw fluid into sample receiving chamber 84. The distance between reference electrode 10 and first isolated portion 52 is from about 2 microns to about 50 microns, typically about 20 microns. In FIG. 1B, the gap A1 and A2 are formed between the peripheral edges of electrode 14 and the peripheral edges of isolated portion 56; gaps A3 and A4 are formed between the edges of isolated portion 54 and the edges of respective electrodes 12 and 14; gaps "A5" and "A6" are formed between the peripheral edges of isolated portion 52 and the peripheral edges of electrode 12 is from about 2 microns to about 50 microns, typically about 20 microns. Each of the gaps A1, A2, A3, A4, A5, A6 and so on is from about 2 microns to about 50 microns, typically 20 microns. While the gaps have preferably the same magnitude in the gap distance, other embodiments can utilize unequal gap distance as long as any one of the gaps is from about 2 microns to about 50 microns.

The width of first isolated portion 52 and second isolated portion 54 is typically from about 120 microns to about 200 microns. When an approximately 20 micron wide line of conductive material is removed by laser ablation to create the electrode and isolated portion patterns on conductive layer 50, less than 10% of the conductive layer 50 on the surface is removed from substrate 5. Removing as little of the conductive material as possible reduces the difference in surface energy between substrate 5 and conductive layer 50 without short-circuiting the test strip electrodes. The advantage is that this results in better adhesion of reagent 22 to conductive layer 50 so that the reagent coating pattern and durability of dry reagent 22 can be controlled.

Conductive layer 50 further includes an antistatic bar 58 at distal end 3 of test strip 90. Antistatic bar 58 helps to dissipate static charge into conductive layer 50 when test strip 90 is in contact with the patient during filling of test strip 90 with blood. Antistatic bar 58 also facilitates uniform reagent coating by minimizing the surface area of exposed substrate 5 that is hydrophobic and facilitates filling of test strip 90 by providing a capillary force to draw fluid into sample receiving chamber 84.

Referring again to FIG. 1C, reference electrode 10, first working electrode 12 and second working electrode 14 are connected to reference contact pad 11, first contact pad 13, and second contact pad 15, respectively, by electrode extensions called "traces." First working electrode trace 8 provides an electrically continuous pathway from first working electrode 12 to first contact pad 13. Similarly, a second working electrode trace 9 provides an electrically continuous pathway from second working electrode 14 to second contact pad 15 and reference electrode trace 7 provides an electrically continuous pathway from reference electrode 10 to reference contact pad 11.

Any electrically conductive material can be used for the conductive layers, such as, for example, Au, Pd, Ir, Pt, Rh, stainless steel, doped tin oxide, carbon, and the like. In one embodiment, the material for the conductive layer may be a carbon ink such as those described in U.S. Pat. No. 5,653,918. In another embodiment, the material for the conductive layer may be a sputtered metal such as gold or palladium at a thickness from about 15 nanometers to about 35 nanometers. In embodiments that use gold as the conductive layer, the sputter conductive layer is typically coated with a hydrophilic material to facilitate reagent coating, such as shown and described in U.S. Pat. No. 6,716,577. An exemplary hydrophilic material includes 2-mercaptoethanesulfonic acid sodium salt at a concentration from about 0.05% to about 0.2%. A surfactant may also be added to the gold coating solution containing hydrophilic material to facilitate even coating. Exemplary surfactants include Pluronic F87 at from about 0.01% to about 0.05% and Pluronic P103 at a concentration from about 0.01% to about 0.05%.

Reagent layer 22 may be disposed on a portion of the conductive layer 50 on the surface, substrate 5 as shown in FIG. 1C. In an embodiment of the present invention, reagent layer 22 may include chemicals such as an enzyme, which selectively reacts with glucose, a mediator and a buffer for maintaining a desired pH. Examples of enzymes suitable for use in this invention may include either glucose oxidase or glucose dehydrogenase. More specifically, the glucose dehydrogenase may have a pyrroloquinoline quinone co-factor (abbreviated as PQQ and may be referred to its common name which is methoxatin). Other glucose dehydrogenase cofactors may be nicotinamide adenine dinucleotide (abbreviated as NAD) or flavin adenine dinucleotide (abbreviated as FAD). Examples of mediator suitable for use in this invention may include either ferricyanide or ruthenium hexamine trichloride ($[Ru^{III}(NH_3)_6]Cl_3$ which may also be simply referred to as ruthenium hexamine). Examples of buffers suitable for use in various embodiments may include phosphate or citraconate. Examples of reagent formulations or inks suitable for use in the various embodiments can be found in U.S. Pat. Nos. 5,708,247 and 6,046,051; published international applications WO01/67099 and WO01/73124.

In one embodiment, the formulation may include a 200 mM phosphate buffer having a pH of about 7 and a ruthenium hexamine mediator concentration ranging from about 5% and greater, preferably ranging from about 10% and greater, and yet more preferably ranging from about 15% to about 20% (percentage based on weight of mediator/volume of buffer). The pH of around 7 was chosen because glucose oxidase has a sufficiently high activity at this pH when using ruthenium hexamine as a mediator. The upper range for ruthenium hexamine was based on its solubility. When the enzyme ink is formulated to have greater than a 20% ruthenium hexamine concentration, solid particles of ruthenium hexamine were present in reagent layer 22 which do not dissolve during testing. The presence of undissolved ruthenium hexamine caused a decrease in the test strip-to-test strip precision. When the enzyme ink is formulated to have less than a 15% ruthenium hexamine concentration, the magnitude of the test current values decreased with the concentration of ruthenium hexamine. In general, it is undesirable for the magnitude of the test current values to be dependent on the concentration of ruthenium hexamine because small changes in ruthenium hexamine concentration will cause variability in the test current values and, in turn, will increase the strip lot-to-lot variability.

In one embodiment, the formulation may have an enzyme activity ranging from about 1500 units/mL to about 50000 units/mL, typically 18000 units/mL. The enzyme activity range may be selected so that the glucose current does not depend on the level of enzyme activity in the formulation so long as the enzyme activity level is within the above stated range. The enzyme activity should be sufficiently large to ensure that the resulting glucose current will not be dependent on small variations in the enzyme activity. For instance, the glucose current will depend on the amount of enzyme activity in the formulation if the enzyme activity is less than 1500 units/mL. On the other hand, for enzyme activity levels greater than 50000 units/mL, solubility issues may arise where the glucose oxidase cannot be sufficiently dissolved in the formulation. Moreover, too much enzyme in the formulation will result in high strip cost. Glucose oxidase may be commercially available from Biozyme Laboratories International Limited (San Diego, Calif., U.S.A.). The glucose oxidase may have an enzyme activity of about 250 units/mg where the enzyme activity units are based on an o-dianisidine assay at pH 7 and 25° C.

Optionally, reagent layer 22 includes a matrix material that aides in retaining the reagent layer 22 on the surface of the conductive layer 50 in the presence of fluid sample and has both hydrophobic and hydrophilic domains. Useful matrix materials include hydrophilic clay, kaolin, talc, silicates, diatomaceous earth or silicas such as Cab-o-Sil® TS-610 or Cab-o-Sil® TS-530 (Cabot Corporation, Boston, USA). While not wishing to be bound by any particular theory, it is believed that silica forms a gel network in the presence of the sample that effectively maintains the coating on the surface of the electrode. Other useful matrix materials include polymeric materials such as sodium alginate, polyethylene glycol, polyethylene oxide, polyvinyl alcohol, polyvinyl acetate, polymeric latex materials, polyethersulfones, acrylic and methacrylic acid polymers; polymers derived from starch, cellulose and other natural polysaccharides, polyamides or collagen. An example of a useful coating composition is disclosed in Example 1 of U.S. Pat. No. 5,708,247. Reagent layer 22 may also optionally include at least one stabilizing agent such as albumin, sucrose, trehalose, mannitol or lactose, an agent such as hydroxyethylcellulose to adjust the viscosity, an antifoam agent such as DC 1500, and at least one wetting agent such as polyvinylpyrrolidone or polyvinyl acetate.

In exemplary embodiments, reagent layer 22 is applied as an even layer to the exposed surface of the electrodes. The thickness of reagent layer 22 prior to contacting the fluid sample should not exceed 50 microns and usually does not exceed 20 microns. To provide an effective coating on the surface of the electrode, the thickness of the layer should not be less than about 5 microns and is usually not less than about 7 microns.

Referring to FIG 1C, spacer layer 60 is typically formed from polyester and is adhered to conductive layer 50 with a heat seal adhesive or a pressure sensitive adhesive.

Top layer 80 is located on distal end 3 of test strip 90 such that a distal portion (i.e. a portion downstream from second working electrode 14) of sample receiving chamber 84 is exposed to atmosphere, creating a vent in test strip 90. In one embodiment, top layer 80 is a polyester material that is adhered to spacer layer 60 with hydrophilic adhesive such as, for example, ARflow 90128 from Adhesives Research Inc.

Top layer 80 is formed from clear polyester to allow a user to visually confirm that sample-receiving chamber 84 is sufficiently filled.

Figure 2A:
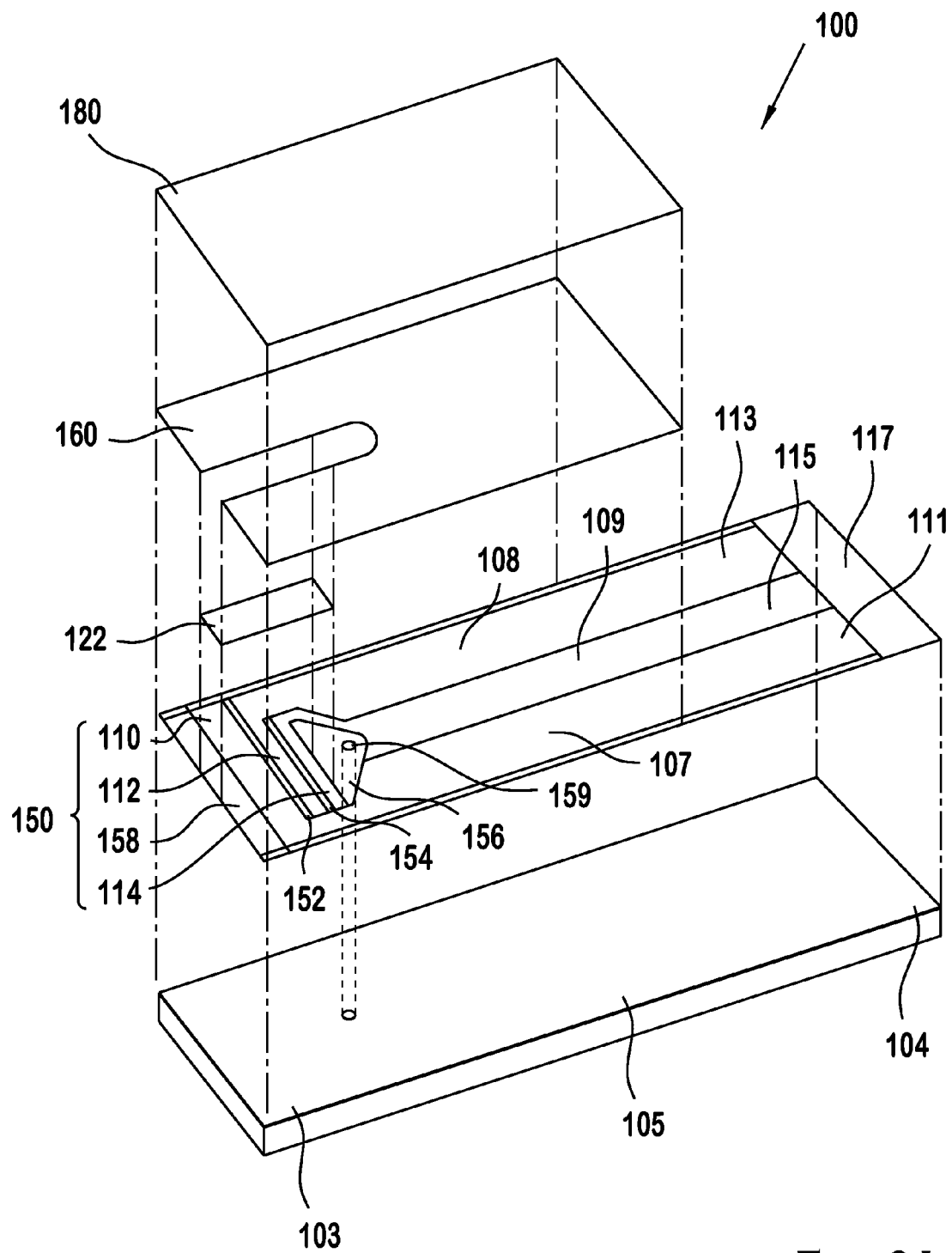
FIG. 2A is a top exploded perspective view of a test strip according to another exemplary embodiment.

Referring now to FIG. 2A, another exemplary embodiment of a test strip 100 is illustrated in exploded perspective view. Test strip 100 includes multiple layers disposed upon a substrate 105. These layers may include a conductive layer 150, a reagent layer 122, a spacer layer 160 and a top layer 180 having a hydrophilic adhesive coating. Test strip 100 may be manufactured in a series of steps in which the conductive layer 150 and reagent layer 122 are sequentially deposited on substrate 105 using, for example, a screen printing process as described in U.S. Pre-Grant Publication No. US20050096409A1 and published International Application Nos. WO2004040948A1, WO2004040290A1, WO2004040287A1, WO2004040285A2, WO2004040005A1, WO2004039897A2, and WO2004039600A2. In an alternative embodiment, an ink jetting process may be used to deposit reagent layer 122 on substrate 105. An example ink jetting process is described in U.S. Pat. No. 6,179,979. Yet another alternative process for depositing reagent 122 onto conductive layer 150 includes a drop-on-demand process. Spacer layer 160 and top layer 180 may be taken from a roll stock and laminated onto substrate 105. In an alternative embodiment, a sputtering process is used to apply conductive layer 150 and patterns are created in conductive layer 150 by laser ablation, laser etching or scribing by mechanical means such that less than 10% or, more typically, less than 6% of conductive layer 150 is removed. Test strip 100 includes a distal end 103 and a proximal end 104 as shown in FIGS. 1A and 1B.

Figure 2B:
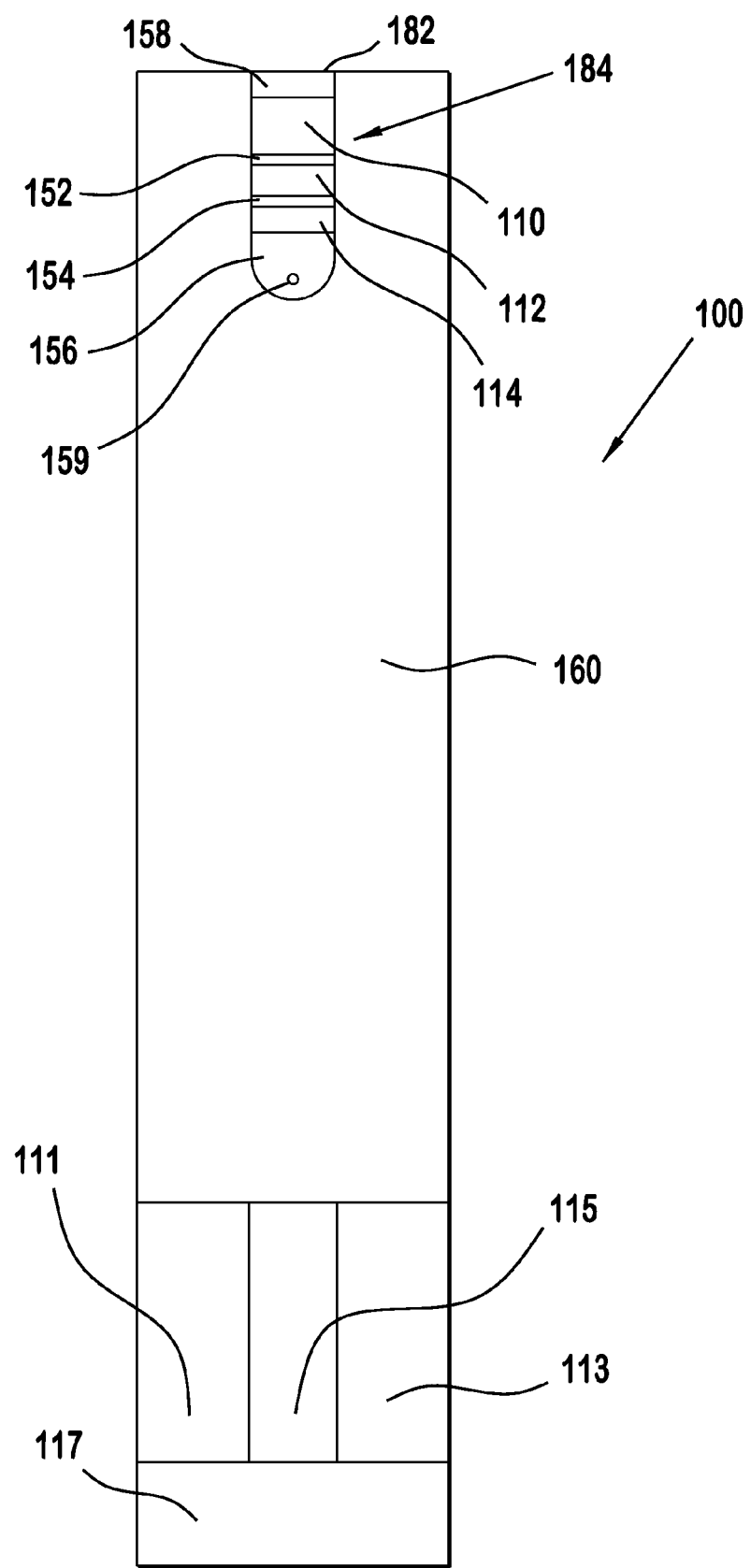
FIG. 2B is a top view of the test strip illustrated in FIG. 2A after it has been assembled.

The fully assembled test strip 100, as shown in FIG. 2B, includes an inlet 182 through which a blood sample may be drawn into a sample-receiving chamber 184. Inlet 182 may be formed by cutting through a distal portion 103 of test strip 100. A blood sample can be applied to inlet 182 to fill sample receiving chamber 184 so that glucose can be measured. The side edges of a U-shaped opening in spacer layer 160 located adjacent to reagent layer 122 each define a wall of sample receiving chamber 184. A bottom portion or "floor" of sample receiving chamber 184 includes a portion of substrate 105 and conductive layer 150. A top portion or "roof" of sample receiving chamber 184 includes distal top layer 180.

The test strip 90 or 100 is manufactured by providing a substrate 5 on which a generally uniform layer of conductive material is deposited, preferably via sputter deposition, over the entire surface(s) of the substrate. Thereafter, laser ablation was utilized to form the conductive pattern 150. In one technique a laser beam movement was controlled to form the electrode patterns including the ablated gaps "A1"; "A2"; "A3"; "A4"; "A4"; "A5"; "A6" and so on in the conductive layer such that these gaps are preferably 50 microns or less and most preferably about 20 microns. In another embodiment, a mask with openings to define the electrode pattern was interposed between an ablation laser and the substrate and conductive layer to ablate the conductive layer at sufficient power and density over a suitable duration such as, for example, less than 100 nanoseconds. Various techniques can be utilized for laser ablation such as, for example, those described in "*Fabrication Techniques and Their Applications to Produce Novel Micromachined Structures and Devices Using Excimer Laser Projection*" by Erol C. Harvey et al., Exitech Ltd., Hanborough Park, Long Hanborough, Oxford, UK, SPIE Vol. 3223, 1997, which is incorporated by reference herein. Regardless of the technique utilized, the conductive layer 150 includes a reference electrode 110, a first working electrode 112, a second working electrode 114, a reference contact pad 111, a first contact pad 113, a second contact pad 115 and a strip detection contact pad 117 can be formed into the conductive or gold layer, as shown in FIGS. 2A and 2B. Reference contact pad 111, first contact pad 113, second contact pad 115 and strip detection contact pad 117 provide electrical connection to a test meter to allow for data and measurement collection.

Conductive layer 150 also includes a first isolated portion 152, a second isolated portion 154 and an optional third isolated portion 156. First isolated portion 152 and second isolated portion 154 facilitate uniform reagent coating by minimizing the surface area of exposed substrate 105 that is hydrophobic. Third isolated portion 156 may be any shape (e.g., triangular) and facilitates filling of test strip 100 by providing a capillary force to draw fluid into sample receiving chamber 184. Third isolated portion 156 also includes an opening 159 therethrough that goes through conductive layer 150 and substrate 105. Opening 159 acts as a vent for test strip 100. The opening 159 can be formed by punching, either via laser or mechanically. Opening 159 can be formed after lamination of all the components of the test strip thereby reducing assembly cost and errors. Opening 159 is preferably a circular opening from about 40 micrometer to about 400 micrometer.

The distance between reference electrode 110 and first isolated portion 152 is from about 2 microns to about 50 microns, typically about 20 microns. The distance between first isolated portion 152 and first working electrode 112 is from about 2 microns to about 50 microns, typically about 20 microns. Likewise, the distance between first working electrode 112 and second isolated portion 154 and the distance between second isolated portion 154 and second working electrode 114 is from about 2 microns to about 50 microns, typically 20 microns. Also, the distance between second working electrode 114 and third isolated portion 156 is from about 2 microns to about 50 microns, typically 20 microns. The width of first isolated portion 152 and second isolated portion 154 is typically from about 120 microns to about 200 microns. When an approximately 20 micron wide line of conductive material is removed by laser ablation to create the electrode and isolated portion patterns on conductive layer 150, less than 10% of conductive layer 150 is removed from substrate 105. Removing as little of the conductive material as possible reduces the difference in surface energy between substrate 105 and conductive layer 150 without short-circuiting the test strip electrodes. The advantage is that this results in better adhesion of the dry reagent to conductive layer 150 so that the reagent coating pattern and durability of the dry reagent pad can be controlled.

Conductive layer 50 or 150 further includes an antistatic bar 158 at distal end 103 of test strip 100. Antistatic bar 158 helps to dissipate static charge into conductive layer 150 when test strip 100 is in contact with the patient during filling of test strip 100 with blood. Antistatic bar 158 also facilitates uniform reagent coating by minimizing the surface area of exposed substrate 105 that is hydrophobic and facilitates filling of test strip 100 by providing a capillary force to draw fluid into sample receiving chamber 184.

Referring again to FIG. 2A, reference electrode 110, first working electrode 112 and second working electrode 114 are connected to reference contact pad 111, first contact pad 113, and second contact pad 115, respectively, by electrode extensions called "traces." First working electrode trace 108 provides an electrically continuous pathway from first working electrode 112 to first contact pad 113. Similarly, a second working electrode trace 109 provides an electrically continuous pathway from second working electrode 114 to second contact pad 115 and reference electrode trace 107 provides an electrically continuous pathway from reference electrode 110 to reference contact pad 111.

Suitable materials which may be used for the conductive layer are Au, Pd, Ir, Pt, Rh, stainless steel, doped tin oxide, carbon, and the like. In one embodiment, the material for the conductive layer may be a carbon ink such as those described in U.S. Pat. No. 5,653,918. In another embodiment, the material for the conductive layer may be a sputtered metal such as gold or palladium at a thickness from about 15 nanometers to about 35 nanometers. In embodiments that use gold as the conductive layer, the sputter gold layer is typically coated with a hydrophilic material to facilitate reagent coating. An exemplary hydrophilic material includes 2-mercaptoethanesulfonic acid sodium salt at a concentration from about 0.05% to about 0.2%. A surfactant may also be added to the gold coating solution containing hydrophilic material to facilitate even coating. Exemplary surfactants include Pluronic F87 at from about 0.01% to about 0.05% and Pluronic P103 at a concentration from about 0.01% to about 0.05%.

Reagent layer 122 may be disposed on a portion of conductive layer 150, substrate 105 as shown in FIG. 2A. In an embodiment of the present invention, reagent layer 122 may include chemicals such as an enzyme, which selectively reacts with glucose and a buffer for maintaining a desired pH. Examples of enzymes suitable for use in this invention may include either glucose oxidase or glucose dehydrogenase. More specifically, the glucose dehydrogenase may have a pyrroloquinoline quinone co-factor (abbreviated as PQQ and may be referred to its common name which is methoxatin). Other glucose dehydrogenase cofactors may be nicotinamide adenine dinucleotide (abbreviated as NAD) or flavin adenine dinucleotide (abbreviated as FAD). Examples of mediator suitable for use in this invention may include either ferricyanide or ruthenium hexamine trichloride ($[Ru^{III}(NH_3)_6]Cl_3$ which may also be simply referred to as ruthenium hexamine). Examples of buffers suitable for use in the various embodiments may include phosphate, or citraconate. Examples of reagent formulations or inks suitable for use in the various embodiments can be found in U.S. Pat. Nos. 5,708,247 and 6,046,051; and published international applications WO01/67099 and WO01/73124.

In one embodiment, the formulation may include a 200 mM phosphate buffer having a pH of about 7 and a ruthenium hexamine mediator concentration ranging from about 5% and greater, preferably ranging from about 10% and greater, and yet more preferably ranging from about 15% to about 20% (percentage based on weight of mediator/volume of buffer). The pH of around 7 was chosen because glucose oxidase has a sufficiently high activity at this pH when using ruthenium hexamine as a mediator. The upper range for ruthenium hexamine was based on its solubility. When the enzyme ink is formulated to have greater than a 20% ruthenium hexamine concentration, solid particles of ruthenium hexamine were present in reagent layer 22 which do not dissolve during testing. The presence of undissolved ruthenium hexamine is believed to cause a decrease in the test strip-to-test strip precision. When the enzyme ink is formulated to have less than a 15% ruthenium hexamine concentration, the magnitude of the test current values decreased with the concentration of ruthenium hexamine. In general, it is undesirable for the magnitude of the test current values to be dependent on the concentration of ruthenium hexamine because small changes in ruthenium hexamine concentration will cause variability in the test current values and, in turn, will increase the strip lot-to-lot variability.

In one embodiment, the formulation may have an enzyme activity ranging from about 1500 units/mL to about 50000 units/mL, typically 18000 units/mL. The enzyme activity range may be selected so that the glucose current does not depend on the level of enzyme activity in the formulation so long as the enzyme activity level is within the above stated range. The enzyme activity should be sufficiently large to ensure that the resulting glucose current will not be dependent on small variations in the enzyme activity. For instance, the glucose current will depend on the amount of enzyme activity in the formulation if the enzyme activity is less than 1500 units/mL. On the other hand, for enzyme activity levels greater than 50000 units/mL, solubility issues may arise where the glucose oxidase cannot be sufficiently dissolved in the formulation. Moreover, too much enzyme in the formulation will result in high strip cost. Glucose oxidase may be commercially available from Biozyme Laboratories International Limited (San Diego, Calif., U.S.A.). The glucose oxidase may have an enzyme activity of about 250 units/mg where the enzyme activity units are based on an o-dianisidine assay at pH 7 and 25° C.

Optionally, reagent layer 122 includes a matrix material that aides in retaining the reagent layer 122 on the surface of conductive layer 150 in the presence of fluid sample and has both hydrophobic and hydrophilic domains. Useful matrix materials include hydrophilic clay, kaolin, talc, silicates, diatomaceous earth or silicas such as Cab-o-Sil® TS-610 or Cab-o-Sil® TS-530 (Cabot Corporation, Boston, USA). While not wishing to be bound by any particular theory, it is believed that silica forms a gel network in the presence of the sample that effectively maintains the coating on the surface of the electrode. Other useful matrix materials include polymeric materials such as sodium alginate, polyethylene glycol, polyethylene oxide, polyvinyl alcohol, polyvinyl acetate, polymeric latex materials, polyethersulfones, acrylic and methacrylic acid polymers; polymers derived from starch, cellulose and other natural polysaccharides, polyamides or collagen. An example of a useful coating composition is disclosed in Example 1 of U.S. Pat. No. 5,708,247. Reagent layer 122 may also optionally include at least one stabilizing agent such as albumin, sucrose, trehalose, mannitol or lactose, an agent such as hydroxyethylcellulose to adjust the viscosity, an antifoam agent such as DC 1500, and at least one wetting agent such as polyvinylpyrrolidone or polyvinyl alcohol.

In exemplary embodiments, reagent layer 122 is applied as an even layer to the exposed surface of the electrodes. The thickness of reagent layer 122 prior to contacting the fluid sample should not exceed 50 microns and usually does not exceed 20 microns. To provide an effective coating on the surface of the electrode, the thickness of the layer should not be less than about 5 microns and is usually not less than about 7 microns.

Referring to FIG. 2A, spacer layer 160 is typically formed from polyester and is adhered to conductive layer 150 with a heat seal adhesive or a pressure sensitive adhesive.

Top layer or cover 180 completely covers spacer layer 160. In one embodiment, top layer 180 is a polyester material that is adhered to spacer layer 160 with hydrophilic adhesive such as, for example, ARflow 90128 from Adhesives Research Inc. Top layer is formed from clear polyester to allow a user to visually confirm that sample-receiving chamber 184 is sufficiently filled.

Figure 3A:
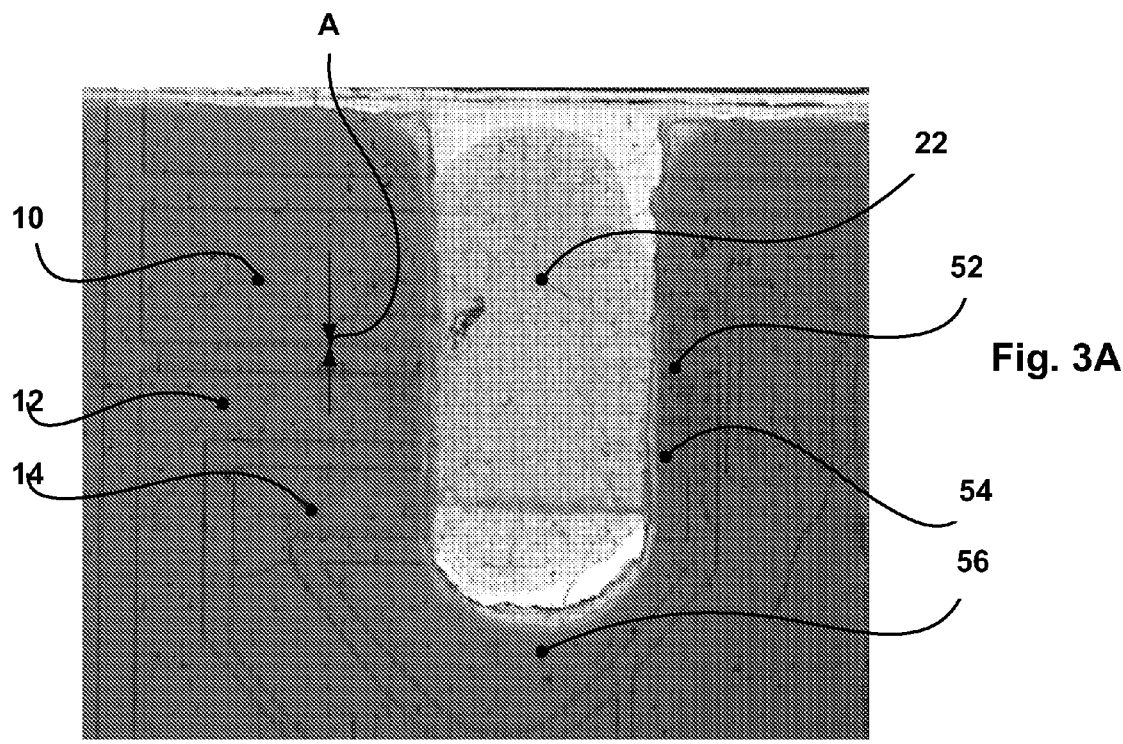
FIG. 3A is a color photomicrograph of a prototype generally in accordance with the design of FIG. 1A that illustrates the favorable distribution of reagent on the electrodes of the test strip.
Figure 3B:
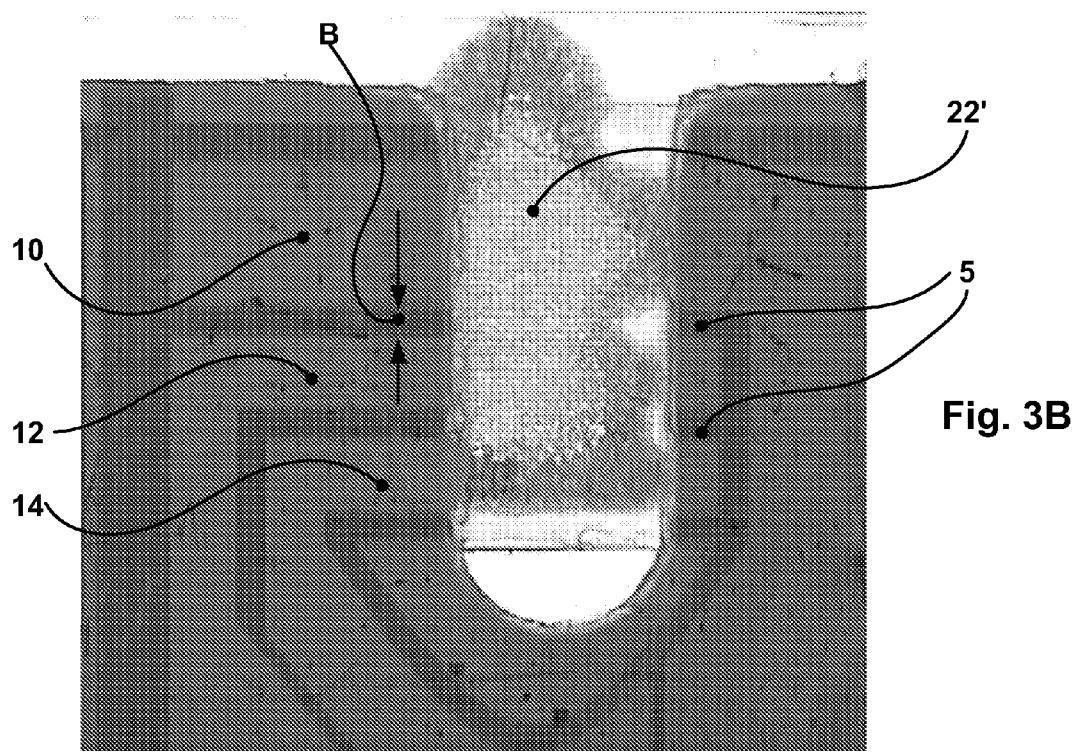
FIG. 3B is a color photomicrograph of another prototype that illustrates a less than favorable distribution of reagent when the gap exposing the substrate is larger than as described herein.

Applicants have discovered that distribution of the reagent on a prototype (FIG. 3A) based on a similar design of FIG. 1A tends to be more uniform as compared to an alternate design (FIG. 3B) that allow for greater exposure of the substrate 5 to the reagent 22, both prototypes being shown here in FIGS. 3A and 3B. Both respective prototypes of FIGS. 3A and 3B were made using the same substrate and conductive material. In particular, rolls of gold sputtered polyester film of about 0.18 millimeter (or about 7 mils) thick were obtained from CP Films. The thickness of the conductive layer (gold in this case) was about 15 nanometers. The film was cut into cards of about 195 mm by 27.5 mm. The conductive layer was patterned to form electrode pattern layer 50 using either of laser scribing or preferably broad field laser ablation, i.e., laser ablation using a mask-like member interposed between the laser and the substrate. Both surfaces of the respective prototypes were treated with MESA and surfactant using an airbrush technique prior to reagent deposition. Specifically, for both types of test strips, the conductive layer 50 was either untreated or was coated with 1, 2 or 4 layers of a solution of 0.1% 2-mercaptoethanesulfonic acid sodium salt (with a concentration given in % based on weight of chemical per volume of solvent) and 0.025% Pluronic F87 (or MESA/F87) to render the surface hydrophilic. A reagent mixture containing about 1% hydroxyethyl cellulose, about 10% ruthenium hexamine Trichloride, about 7.2% glucose oxidase, about 0.033% Pluronic P103, about 0.017% Pluronic F87, and about 0.2M phosphate buffer of pH 6.9 was deposited on the electrode layer via a suitable non-contact drop-on-demand system such as, for example, BioDot. The card was thereafter dried using an Infrared heater at about 60° Celsius for about 3 minutes. After drying, the card was laminated with a spacer and a hydrophilic top tape to form an array of glucose sensors.

In the first prototype of FIG. 3A, the gap "A" between the edges of any of the electrodes 10, 12, or 14 and the edges of proximal electrically isolated islands 52, 54, or 56 is about 20 microns. In contrast, the gap "B" in the alternate prototype (FIG. 3B) is about 200 microns, which allows for more of the substrate surface 5 to be exposed. The difference in gap spacing A (~20 microns) versus B (~200 microns) leads to what is believed to be a very surprising result once reagent is deposited over the electrode patterns in both prototypes. Comparing both FIGS. 3A and 3B, one can see this surprising result. In FIG. 3A, the reagent 22 can be seen as more uniform than the reagent 22' in FIG. 3B. Applicants believe that the lower the amount of conductive material removed in the prototype of FIG. 3A allowed for greater surface uniformity with less exposure of the underlying substrate as compared to FIG. 3B. It was also discovered that uniform reagent deposition led to increased uniformity in the distribution of the analytical fluid. Consequently, it is believed that uniform distribution of the reagent in the prototype of FIG. 3A allows for greater precision of the analyte measurement process.

EXAMPLE

Precision Study

To validate this premise, a precision study was conducted comparing a prototype of the test strip shown in FIGS. 1A-1C with electrically isolated islands ("CI") 52 and 54 (or "CI test strip") to prototype of test strips that did not include electrically isolated islands 52 and 54 (or non-CI test strip). The width of the conductive islands 52 and 54 on CI test strips was 140 microns and the distance between the reference or working electrodes 10 or 12 and the conductive island was 30 microns. For the non-CI test strips, the distance between the electrodes was 200 microns.

In order to test only the background current of test strips, both the CI test strips and non-Cl test strips were assembled with all but reagent layer 22. The method of testing included applying a 2 second open circuit followed by a 3 second 400 mV potential to the test strip. At 2 seconds a solution of 151 mM potassium ferricyanide/19 mM potassium ferrocyanide was applied to each test strip and the average current at 5.0 seconds was measured. The precision results (or CV % of current) are shown in Table 1.

TABLE 1

| Case | Avg. current @ 5.0 s | CV % of current | Number of replicates |
|---|---|---|---|
| CI Untreated gold | 19.85 | 3.66 | 24 |
| CI 1x MESA/F87 | 19.576 | 3.04 | 20 |
| CI 2x MESA/F87 | 19.83 | 2.21 | 20 |
| CI 4x MESA/F87 | 20.22 | 2.70 | 19 |
| Non-CI Untreated gold | 19.185 | 6.04 | 19 |
| Non-CI 1x MESA/F87 | 20.39 | 3.81 | 16 |
| Non-CI 2x MESA/F87 | 20.66 | 5.47 | 21 |
| Non-CI 4x MESA/F87 | 20.61 | 4.44 | 18 |

The data of Table 1 indicate that the CV % of current for the CI test strips is significantly improved in comparison to the non-CI test strips.

Figure 4:
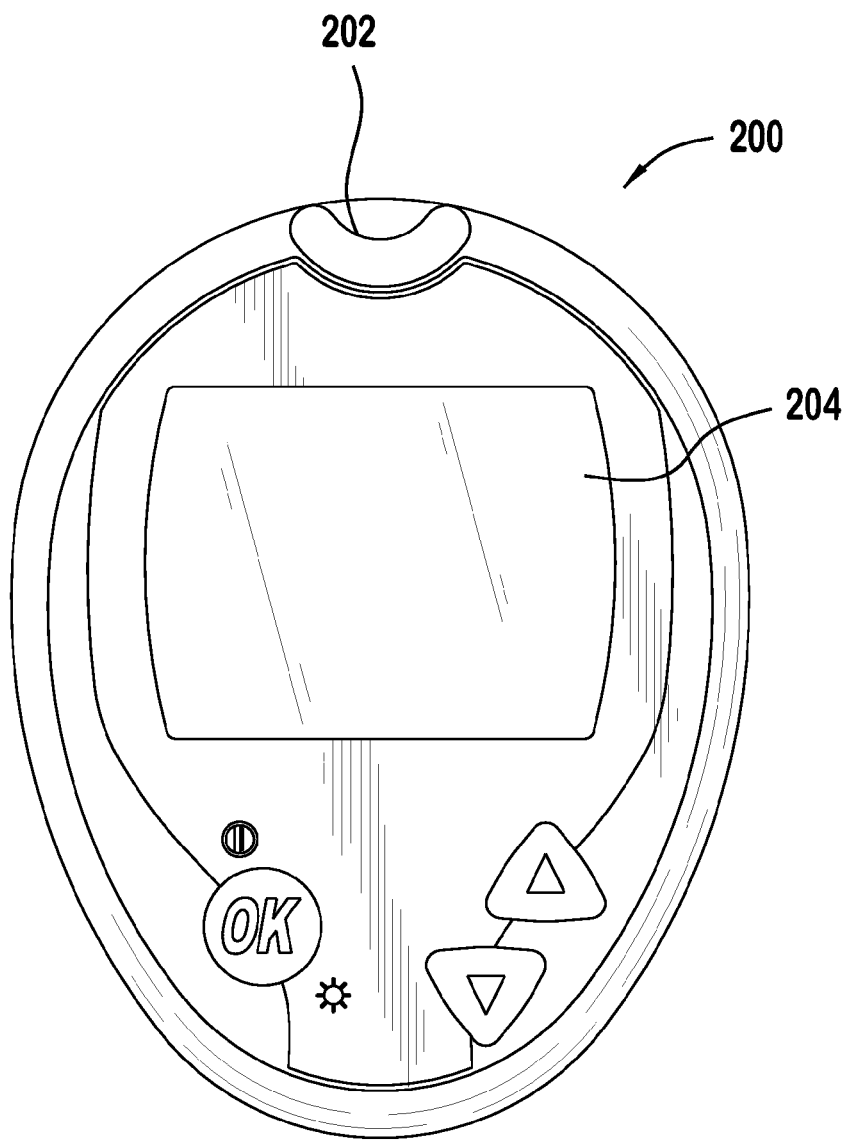
FIG. 4 is a top view of an exemplary meter that may be used with the test strip shown in FIGS. 1A-1E and FIGS. 2A-2B.

Referring generally now to FIG. 4, test strip 90 (or test strip 100) shown in FIGS. 1A-1C (or FIGS. 2A-2B) is typically coupled to a meter 200 or other electrical device by an electrical connector 202 which is configured to couple with and contact the end of test strip 90 at contact pads 11, 13, 15 and 17. Meter 200 typically includes a potentiostat or other component to provide a potential and/or current for the electrodes of test strip 90. The meter also typically includes a processor (e.g., a microprocessor or hardware) for determining analyte concentration from the test strip signals. The meter also includes a display 204 for displaying results determined from the test strip signals including, for example, analyte concentration, rate of change of analyte concentration, and/or the exceeding of a threshold analyte concentration (indicating, for example, hypo-or hyperglycemia).

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. An analyte test strip comprising:
a substrate having a generally planar surface that extends from a first end to a second end;
an electrically conductive material disposed on the generally planar surface to define a plurality of electrodes spaced apart from each other;
an electrically isolated island portion of the electrically conductive material disposed between at least two of the plurality of electrodes; and
a reagent layer at least partially covering the plurality of electrodes and the electrically isolated island portion.

2. The test strip of claim 1, in which the width of the electrically isolated island portion is from about 120 microns to about 200 microns.

3. The test strip of claim 1, in which the distance between one of the plurality of electrodes and the electrically isolated island portion and the distance between the electrically isolated island portion and another of the plurality of electrodes is from about 2 microns to about 50 microns.

4. The test strip of claim 1, further including another electrically isolated island portion of electrically conductive material distal to both the first end and one of the plurality of electrodes and configured such that capillary action is assisted during filling of the test strip with a fluid sample deposited on the test strip.

5. The test strip of claim 1, in which the plurality of electrodes and the electrically isolated island portion of electrically conductive material is coated with a hydrophilic material.

6. A test strip for measuring a concentration of an analyte in a fluid sample, the test strip comprising:
a substrate;
a reference electrode disposed on the substrate;
a first working electrode disposed on the substrate proximate the reference electrode;
a second working electrode disposed on the substrate proximate the first working electrode;
a first electrically isolated island portion of electrically conductive material located proximal to one of the first and second working electrodes and distal to the reference electrode; and
a reagent layer at least partially covering the reference electrode, the first working electrode, the second working electrode and the electrically isolated island portion.

7. The test strip of claim 6, wherein the first electrically isolated island portion comprises a substantially triangular shape portion.

8. The test strip of claim 6, further comprising a vent opening through the electrically isolated island portion of electrically conductive material and through the substrate.

9. The test strip of claim 6, in which a width of the electrically isolated island portion is from about 120 microns to about 200 microns.

10. The test strip of claim 6, in which the distance between the reference electrode and the first electrically isolated island portion and the distance between the first electrically isolated island portion and the working electrode is from about 2 microns to about 50 microns.

11. The test strip of claim 6, further including a second electrically isolated island portion of electrically conductive material and wherein the first electrically isolated island portion is between the reference electrode and the first working electrode and the second electrically isolated island portion is between the first working electrode and the second working electrode, and in which the reference electrode, the first working electrode, the second working electrode, the first electrically isolated island portion and the second electrically isolated island portion are coated with a hydrophilic material.

12. The test strip of claim 11, in which the hydrophilic material comprises 2-mercaptoethanesulfonic acid sodium salt.

13. A method of making an analyte test strip, the method comprising:
depositing a layer of a conductive material on a substrate;
removing selective portions of the layer of conductive material to define a plurality of electrodes and at least one electrically isolated island portion of the conductive material separated from any of the plurality electrodes at a distance of less than about 50 microns to electrically isolate the at least one electrically isolated island portion from the electrodes; and
depositing a reagent layer at least partially covering the plurality of electrodes and the at least one electrically isolated island portion.

14. The method of claim 13, in which the removing comprises broad field laser ablating the layer of conductive material over a duration of less than 100 nanoseconds.

15. The method of claim 13, further comprising coating the plurality of electrodes and the at least one electrically isolated island portion with a layer of material to render such surfaces hydrophilic.

16. The method of claim 13, further comprising attaching a cover layer to the layer of conductive material.

17. The method of claim 16, further comprising forming a chamber defined by a surface of the reagent layer, a wall of the cover layer and a top cover over the chamber.

18. The method of claim 17, in which the removing step removes less than 10% of the layer of conductive material to form the plurality of electrodes and the at least one electrically isolated island portion.

19. The method of claim 18, further comprising puncturing an orifice through the substrate and the layer of conductive material.

* * * * *